United States Patent [19]

Pagel

[11] Patent Number: 4,503,703

[45] Date of Patent: Mar. 12, 1985

[54] MOLECULAR GAS DETECTOR AND ANALYZER

[76] Inventor: Hayes L. Pagel, 2185 W. Hiwatha Ave., Anaheim, Calif. 92804

[21] Appl. No.: 413,743

[22] Filed: Sep. 10, 1982

[51] Int. Cl.³ ............................................ G01N 15/02
[52] U.S. Cl. ............................................ 73/23; 73/28
[58] Field of Search ................................ 73/23, 24, 28

[56] References Cited

U.S. PATENT DOCUMENTS

| 2,521,634 | 9/1950 | Janssen et al. | 73/24 |
| 3,266,291 | 8/1966 | King, Jr. | 73/23 |
| 3,561,253 | 2/1971 | Dorman | 73/28 |
| 3,715,911 | 2/1973 | Chuan | 73/28 |

Primary Examiner—Stephen A. Kreitman
Attorney, Agent, or Firm—William C. Babcock

[57] ABSTRACT

An apparatus in which a current of air is directed across a surface of a substance of unknown identity to have molecules of the latter entrained therewith. The molecules are attracted electrostatically to the surface of a piezoelectric element to cause microscopic vibrations of the element. The microscopic vibrations result in the piezoelectric element emitting a minute voltage at a like frequency that is subsequently amplified. The amplified voltage is used to produce pulsed sound waves that are directed onto a resilient diaphram to vibrate the latter, and the mechanical energy of the diaphram being transferred to the piezoelectric element to amplify the voltage emitted. The amplified voltage is of sufficient magnitude to actuate an oscilloscope or recording computer to provide a distinctive pattern that is used to identify the unknown substance.

12 Claims, 9 Drawing Figures

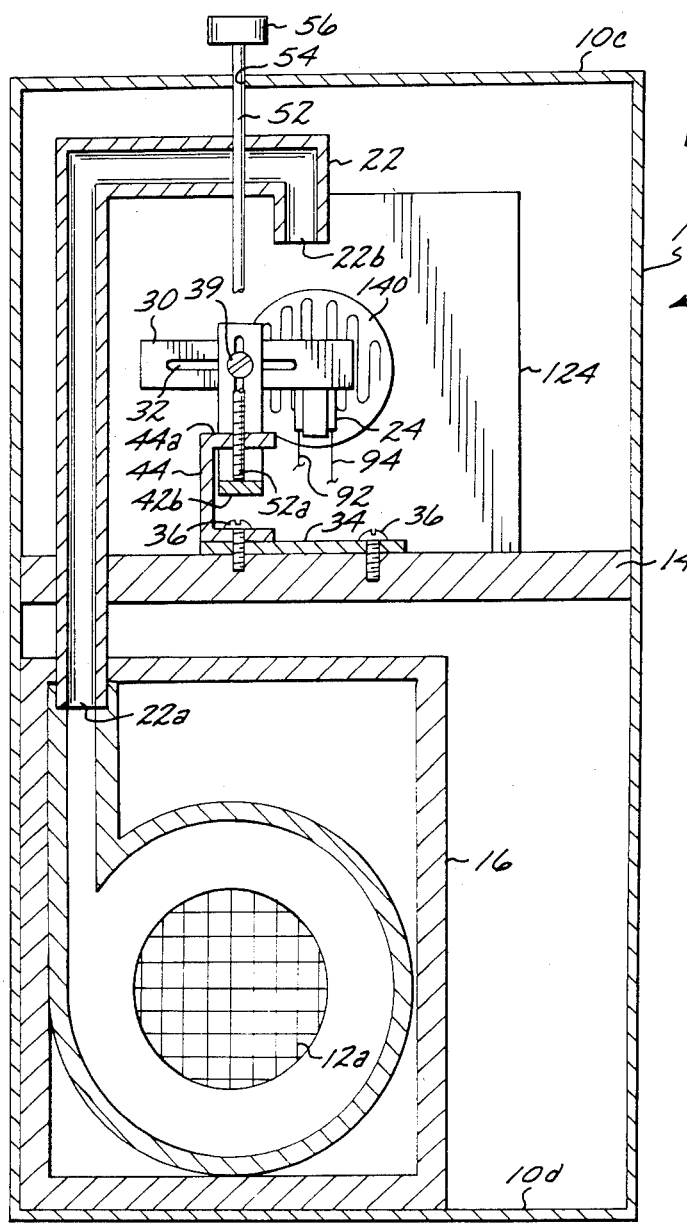
FIG. 3
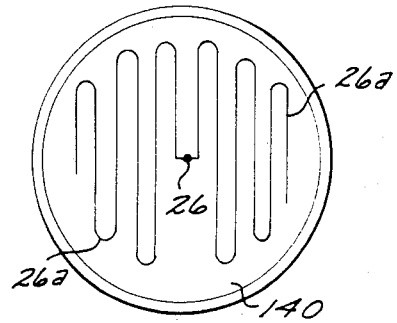
FIG. 4
FIG. 5
FIG. 6
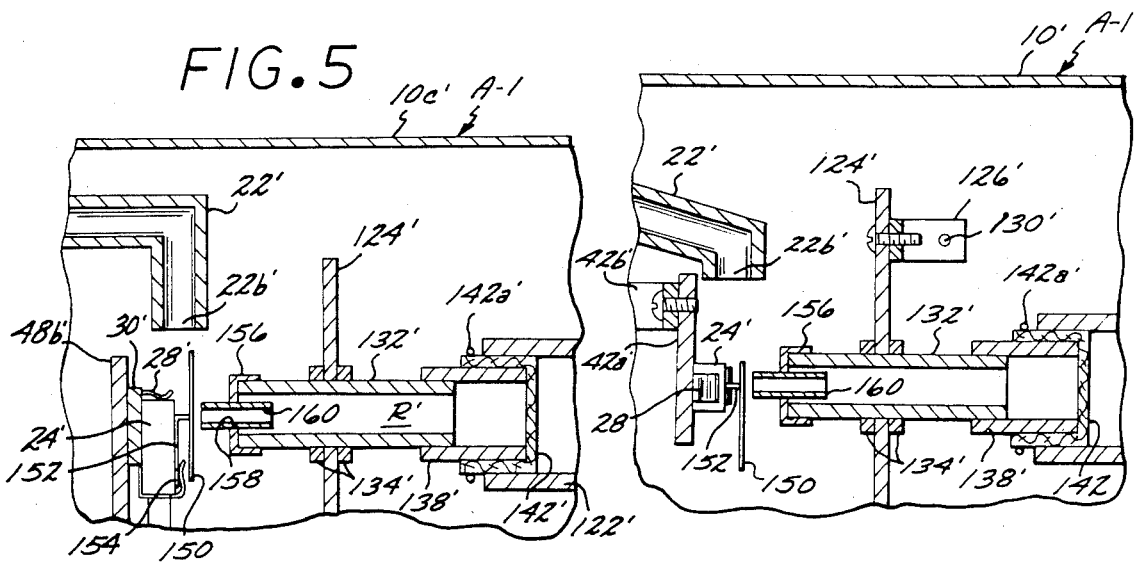

4,503,703

MOLECULAR GAS DETECTOR AND ANALYZER

BACKGROUND OF THE INVENTION

1. Field of the Invention

Molecular Gas Detector and Analyzer.

2. Description of the Prior Art

In the past, detection and identification of an unknown substance not common to the ambient atmosphere has been attained either by chemical means or by the use or spectroscopes and the like that are not only expensive, but time consuming to use, and require the services of highly skilled personnel.

A major object of the present invention is to provide an apparatus that is compact, may be portable or stationary, is simple and easy to use, detects and identifies an unknown substance by utilizing the unbalanced molecular characteristics thereof that exist at the interface of the unknown substance with the ambient atmosphere, and the unbalanced molecular characteristic being specific and unique for one substance only.

A further object of the invention is to provide an apparatus in which a stream of air is directed over the surface of the unknown substance, if the latter is a liquid or solid, or mixed with a substance if the substance is a gas, with the stream of air after being exposed to the unknown substance being pressurized and directed onto a piezoelectric element in a confined space where molecules of the unknown substance collect on the surface of the piezoelectric element and subject the latter to mechanical pulses that result in pulses of electric energy being emitted therefrom that are subsequently amplified and fed back to the piezoelectric element for the latter to regenerate an electric signal of sufficient magnitude to be registerable on an oscilloscope or a recording read out.

A further object of the invention is to supply an apparatus in which a visual or printed pattern is obtained of an unknown substance, which pattern is unique and specific to that substance alone, and permits the identification of the unknown substance by comparing the pattern obtained with the patterns of substances the identities of which are known.

A still further object of the invention is to supply an apparatus in which the molecular activity of a substance at the interface of the ambient atmosphere may be studied in detail by obtaining a visual or printed pattern thereof, and a pattern capable of being modified to various levels by settings on the apparatus to demonstrate frequency bands, phase shifts, pulse frequencies, cross over modes, total harmonics, and overtones and the like.

These and other objects and advantages of the invention will become apparent from the following description thereof, of first and second forms and the method of using the apparatus to obtain the results of which it is capable.

SUMMARY OF THE INVENTION

An apparatus and method of using the same to detect and identify a substance not common to the ambient atmosphere, by directing a stream of air relative to the substance for the molecular vapor of the latter to intermix therewith, and such vapor intermixing occuring irrespective of whether the substance is a solid, liquid or gas. The stream of intermixed air and vapor is pressurized and directed onto a piezoelectric element situated within a confined space.

The piezoelectric element has force receiving means protruding therefrom. Molecules of the unknown substance collect on the surface of the piezoelectric element where they subject the element to minute mechanical vibrations that result in the element emitting minute pulses of electric energy that flow to a voltage amplifier of conventional design.

The output of the amplifier powers a loud speaker amplifier to which the cone of the speaker responds. The pulsating sound from the cone is directed through a conversion tube to a second element operatively associated with the force receiving means to vibrate the latter and subject the surface of piezoelectric element to pulses of mechanical energy.

Such pulses of mechanical energy amplify the mechanical energy of the molecular disturbance on the surface of the piezoelectric element, which results in the voltage output of the piezoelectric element being substantially increased. The amplified voltage from the amplifier may be used to actuate either an oscilloscope or a recording computer read out. Each substance at the interface with the ambient atmosphere has an unbalanced molecular pattern that is specific to it alone. This pattern or a modified form thereof is produced on the oscilloscope or recording computer read out, and permits the identification of the unknown substance by comparing the obtained pattern thereof on the oscilloscope or recording computer read out with patterns of substances, the identity of which are already known.

BRIEF DESCRIPTION OF THE DRAWINGS

FIG. 3 is an end elevational view of the first form of the invention;

FIG. 4 is an end elevational view of the force receiving grid;

FIG. 5 is a longitudinal cross sectional view of a modification that may be made to the conversion tube piezoelectric element and force receiving grid of the invention shown in FIG. 1;

FIG. 6 is a top plan view of the modification shown in FIG. 5;

DESCRIPTION OF THE PREFERRED EMBODIMENTS

Figure 1:
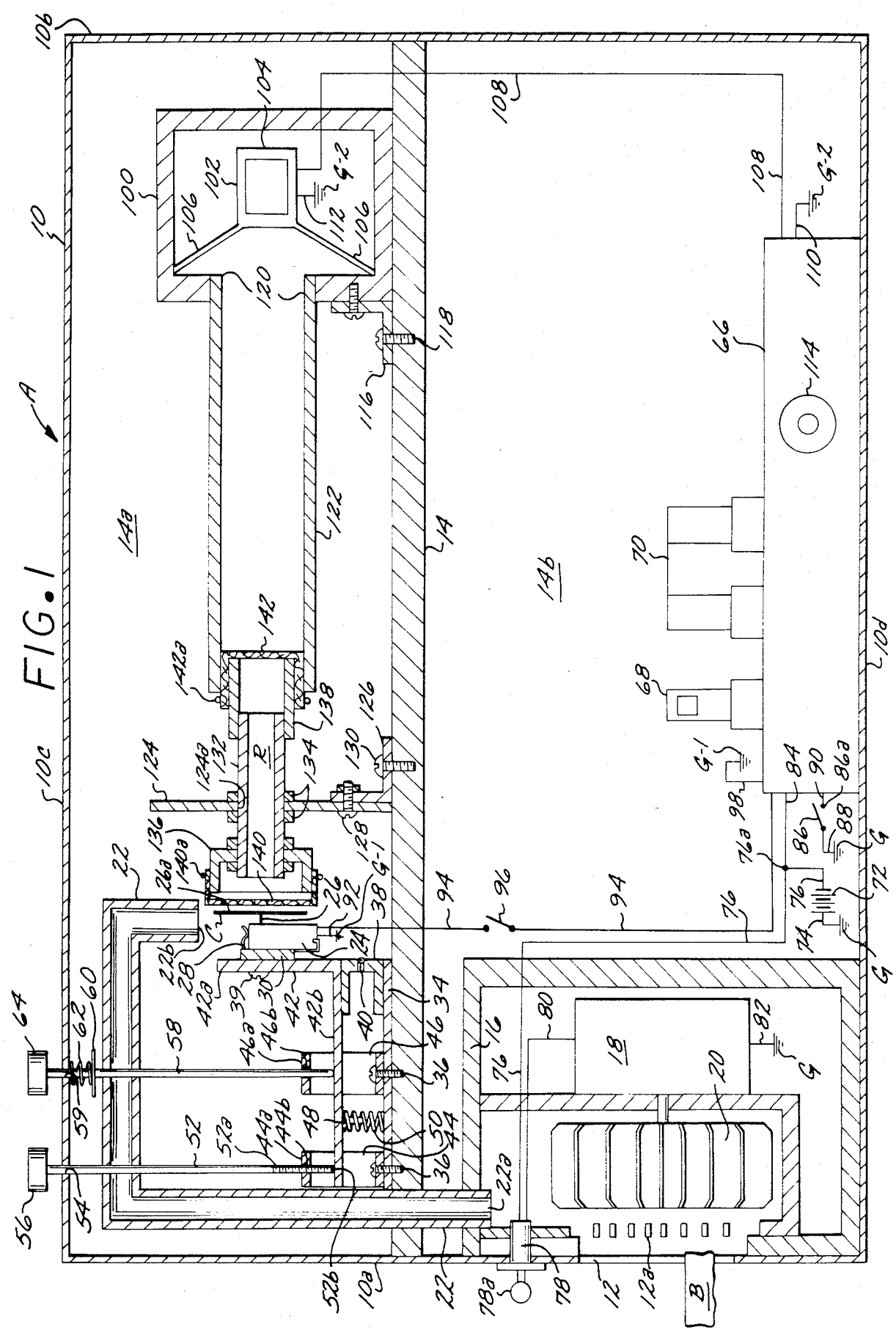
FIG. 1 is a combined side elevational and longitudinal cross sectional view of a first form of the apparatus.
Figure 2:
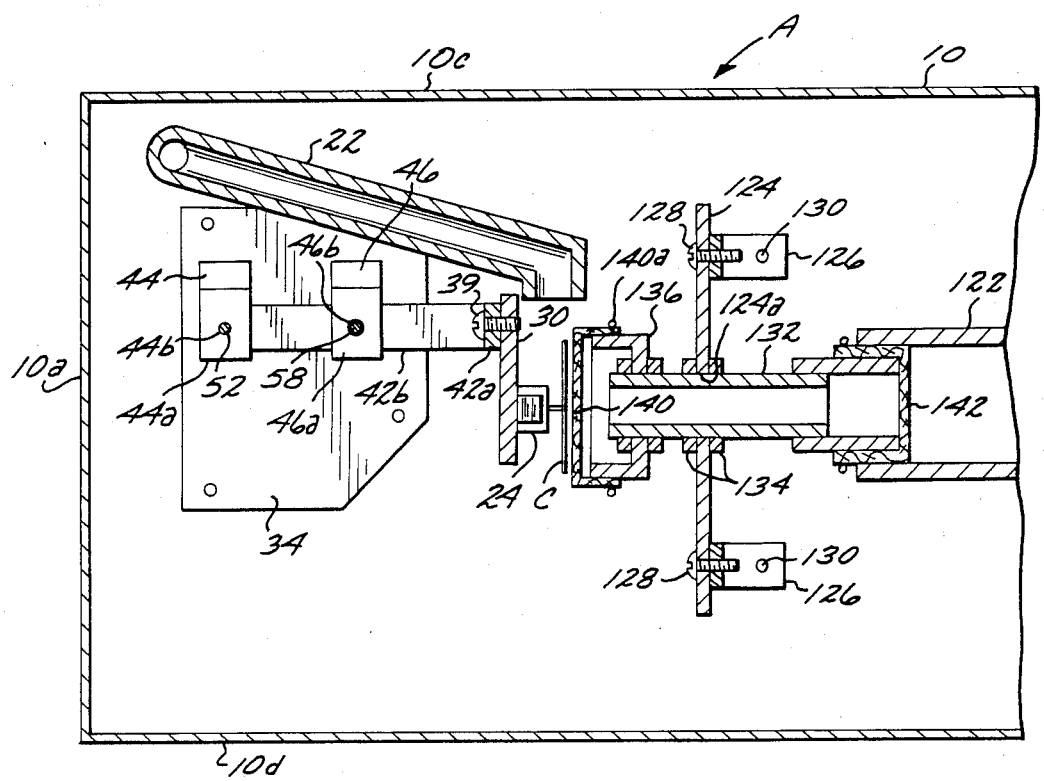
FIG. 2 is a combined longitudinal cross sectional view and top plan view of a portion of the first form of the invention taken on the line 2—2 of FIG. 1.
Figure 7:
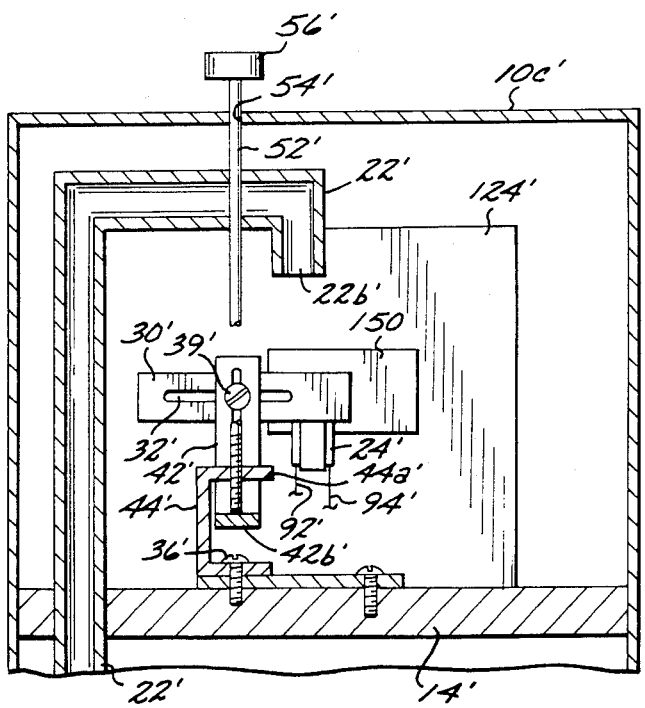
FIG. 7 is an end elevational view of the modification shown in FIGS. 5 and 6.
Figure 8:
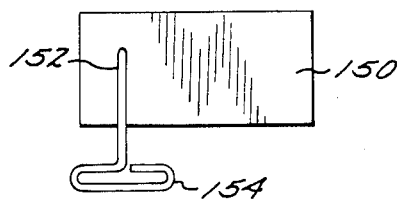
FIG. 8 is an end elevational view of the force receiving reed utilized in the modification shown in FIG. 7.
Figure 9:
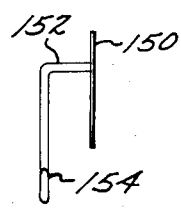
FIG. 9 is a side elevational view of the force receiving member illustrated in FIG. 8.

First form A of the invention is shown in FIGS. 1 and 4 inclusive wherein it will be seen that it includes a housing 10 having a forward end wall 10a, rear end wall 10b, a top 10c, and bottom 10d. An opening 12 is formed in the forward end wall 10a in the lower portion thereof and is covered by a screen 12a. A body of an unknown substance B to be identified is placed adjacent the opening 12 as shown in FIG. 1.

A horizontal shelf 14 sub-divides the interior of the housing 10 into an upper portion 14a and lower portion 14b. The lower portion 14b has a blower housing 16 situated therein adjacent the forward end wall 10a and in communication with the opening 12. An electric motor 18 is situated within the blower housing 16 and when electrically energized rotates an impeller 20. An inverted J shaped tube 22 extends upwardly from the blower housing 16 and is in communication with the interior thereof. The tube 22 has a pressurized inlet 22a and a pressurized air outlet 22b as shown in FIG. 1.

A piezoelectric element 24 is shown in FIG. 1 that has a force receiving grid C extending outwardly therefrom, which grid includes a wire 26 that develops into a number of force receiving loops 26a. The piezoelectric element 24 may be a pick-up such as used on a phonograph. The piezoelectric element 24 is removably supported by a resilient clip assembly 28 that is secured to an end portion of a horizontal cross piece 30, which cross piece has an elongate slot 32 therein.

In FIG. 1 it will be seen that a base plate 34 is secured to the upper surface of the shelf 14 adjacent the forward end wall 10a. The base plate 34 is secured to the shell 14 by screws 36. The base plate 34 has a bracket 38 secured thereto, which bracket on the upper end is provided with pivotal means 40 that are attached to a member 42. The member 42 includes a vertical arm 42a and horizontal arm 42b that extends towards the forward end wall 10a as shown in FIG. 1. The slot 32 is adjustably engaged by a screw 39 secured to arm 42a to permit movement of the cross piece relative to arm 42a.

In FIG. 1 it will be seen that a first guide 44 is provided that is secured to the base 34 by one of the screws 36 and the guide includes a horizontal leg 44a that is disposed above the horizontal arm 42b, which horizontal arm has a vertical tapped bore 44b formed therein. A second guide 46 is also provided that is secured to the base 34 and has a horizontal leg 46a disposed above the arm 42b, and the leg 46a having a vertical bore 46b formed therein. A pin 48 extends downwardly from the arm 42b and is encircled by a compressed helical spring 50 that at all times tends to pivot the member 44 in a clockwise direction. The degree of pivotal movement in a clockwise direction is limited by the position of the lower end of a first rod 52.

In FIG. 1 it will be seen that the first elongate rigid rod 52 extends downwardly through an opening 54 in the top 10c of housing 10, with the rod including a lower threaded end portion 52a. The threaded portion 52a engages the tapped bore 44b and when the rod is rotated by a handle 56, a lower end 52b of the rod exerts a downward force on the arm 42b that tends to rotate the member 42 in a counter clockwise direction as viewed in FIG. 5. Rod 52 serves as a stop to limit clockwise rotation of member 42 and as a means for imparting counter clockwise rotation thereto. Such counter clockwise rotation of the member 44 is resisted by the upward force exerted by the compressed spring 50.

The second rod 58 extends downwardly through an opening 59 in the top 10c and has a plate 60 mounted thereon. A compressed helical spring 62 encircles the second rod 58, with the ends of the spring being in abutting contact with the top 10c and the plate 10. The rod 58 is slidably mounted in the vertical bore 46b of the horizontal leg 46a as shown in FIG. 1, with the rod having a lower end that is in contact with the arm 42b. The upper end of the rod 58 has a handle 64 mounted thereon as shown in FIG. 1. The purpose of the rods 52 and 58 will later be explained.

Am amplifier 66 is shown as being disposed within the housing 10 in FIG. 1, and has a voltage output that is recordable on either an oscilloscope 68 or a recording computer read out 70. For simplicity of explanation the oscilloscope 68 and recording computer read out 70 are shown adjacent the amplifier 66, but in actuality the oscilloscope and recording computer read out 70 would be situated outside the housing 10.

A source of electric power 72 is provided that may be either a domestic electric outlet, a battery or the like. The source of electric power 72 has one terminal thereof connected by a conductor 74 to ground G. The other terminal of the source of electric power 72 is by a conductor 76 connected to one terminal of electric switch 78 that is illustrated as mounted on the forward end wall 10a and manually actuated by a handle 78a.

The second terminal of the electric switch 78 is connected by a conductor 80 to the electric motor 18, with the other terminal of the motor having a conductor 82 extending therefrom to ground G. Closing of the switch 78 actuates the motor 18 to drive the impeller 20. Electric conductor 84 extends from a junction point 76a in the conductor 76 to one terminal of the amplifier 66, with the second terminal of the amplifier being connected by a conductor 90 to a contact 86a of a switch 86, which switch by a conductor 88 is connected to ground G. When the switch 86 is in the closed position the amplifier 66 is electrically energized.

When the switch 78 is closed, the motor 18 is electrically energized to drive the impeller 20. The impeller 20 draws air through the opening 12 and across the molecularly active surface of the body B, with the air stream and molecular vapor intermixed with one another being discharged upwardly through the tube 22 to flow over the piezoelectric element 24. As such flow takes place molecules of the substance B are electrostatically attracted to the exterior surface of the piezoelectric element 24 and imparts minute vibrations thereto. Vibrations of the piezoelectric element 24 result in a minute voltage being emitted therefrom which voltage has a frequency that is related to the activity of the molecules deposited on the exterior surface of the element 24.

The minute voltage from the piezoelectric element 24 flows through a circuit that includes a conductor 94 that has a switch 96 therein to a first input terminal of the amplifier 66. The second terminal of the piezoelectric element 24 is connected by a conductor 92 to ground G-1. The second imput terminal of the amplifier 66 is by a conductor 98 connected to ground G-1. The imput of voltage from the piezoelectric element 24 is amplified by the amplifier 66 to flow through an electric circuit that includes a conductor 108 and a second conductor 110 that is connected to a ground G-2.

The shelf 14 adjacent the rearward end wall 10b has a housing 100 supported thereon in which a loud speaker 102 is disposed that has an armature 104 and a cone 106. The conductor 108 is connected to one terminal of the armature 104, with the other terminal of the armature being connected to a conductor 112 that extends to ground G-2.

The amplified voltage from the amplifier 66 actuates the armature 104 of the loud speaker 102. The housing 100 is held in a fixed relationship with the shelf 14 by a bracket 116 that is secured to the housing, and the bracket also being secured to the shelf 14 by a screw or screws 118. The mouth 120 of the loud speaker 102 is in communication with a horizontal speaker outlet tube 122 that extends towards the forward end wall 10a as shown in FIG. 1.

In FIG. 1 it will be seen that a vertical plate 124 is provided that is situated above the shelf 14 in the upper portion 14a of the housing 10 and to the left of the speaker outlet tube 122. The vertical plate 124 is secured to an L shaped bracket 126 by screws 128. The bracket is secured to the upper surface of the shelf 14 by screws 130. The plate 124 has a horizontal transverse tapped opening 124a therein. An externally threaded tube 132 extends through the opening 124a and is removably held in a fixed position on the plate 124 by a pair of lock nuts 134. The tube 134 supports a forward ring 136 and a rearward ring 138 as shown in FIG. 1, with the forward ring having an internal diameter that is substantially greater than that of the rearward ring 138. The forward and rearward rings have forward and rearward resilient membranes 140 and 142 spanning the outer extremities thereof, and the membranes being removably held on the rings by forward and rearward clamps 140a and 142a.

The use and operation of the first form A of the invention is as follows. The switch 78 is closed to cause the motor 18 to drive the impeller 20. The rotating impeller 20 draws a stream of air over the body of the unknown substance B, and surface active molecules of the substance are entrained with the stream of air. The stream of air and entrained molecules are pressurized to flow through the tube 22 downwardly over the piezoelectric element 24. The entrained molecules are attracted electrostatically to the surface of the piezoelectric element 24 and the grid C. The switch 78 is now returned to an open position to terminate further flow of air and molecules through the tube 22.

Molecules on the surface of the piezoelectric element 24 subject the latter to minute vibrations, which vibrations result in the element 24 generating a minute voltage that has a frequency that is related to that of the molecules on the surface of the element 24. When the switches 96 and 86 are placed in closed positions, this minute voltage flows to the amplifier 66 to be amplified to a substantial magnitude. The amplified voltage output of the amplifier 66 is at the same frequency as the minute voltage imput.

Amplified voltage from the amplifier 66 flows to the armature 104 of loud speaker 102 to actuate cone 106 to emit sound waves at a frequency that is related to the frequency of the amplified voltage. The sound waves travel longitudinally down the tube 122 to impinge on the rearward diaphram 142 to cause the same to vibrate. The tube 132, forward and rearward rings 136 and 138, and forward and rearward diaphrams 140 and 142 cooperate to define a confined resonator cavity R that is filled with air. As the rearward diaphram 142 vibrates, the air in the resonator cavity R alternately increases and decreases in pressure, to cause vibration of the forward diaphram 140. The rearward diaphram 142 is of substantially less transverse cross section than the forward diaphram 140, and as a result the increase and decrease in pressure in the resonator cavity does not result in a linear relationship between the vibrating diaphram 142 and the forward diaphram 140.

In summary, the tube 132 has two functions, the first function is to convert a linear wave front to a non-linear wave front. The second function is to magnify and spread the details of the sound wave front. In the first function, the change of frequency from linear to non-linear is caused by the unequal size of the membranes 142 and 140. The smaller and rearwardly disposed membrane 142 vibrates much faster than the larger forwardly disposed membrane 140.

The second function of the tube 132 is that a sealed membrane in motion becomes a convex-convex sound lens by reason of motion in compression and expansion of molecular dimensions, changing the focal length. In a sealed tube by the Bermoulli effect, the sound stream is thrown back and forth between a small and large aperture, from a small image to a larger image. In the present instance as the sound wave is thrown upon the larger membrane 140, the larger membrane becomes a convex-convex sound lens, and it spreads the wave image on the outside surface of the membrane and magnifies the details of the image.

The forward surface of the membrane 140 is in contact with the loops 26a of the membrane C as shown in FIG. 4. The grid C conforms substantially to the forward surface of the membrane 140. At the center of the grid C, the wire 26 is in contact with the piezoelectric element 24, which element may be a part of a conventional phono-pickup cartridge in which the exterior surface of the piezoelectric crystal is available to have the entrained molecules deposited thereon. The pressure of the loops 26a of the grid C on the membrane 140 is regulated by rotation of the first rod 52 to pivot the spring loaded member 42 either clockwise or counter clockwise. Clockwise rotation of the member 42 increases the pressure of grid C on membrane 140, and counterclockwise rotation lessens the pressure.

The purpose of the grid C is to pick up in detail the molecular vibrations of the forward membrane 140 and transfer these vibrations to the piezoelectric element 24.

Vibration of the grid C results in an intensified mechanical disturbance on the surface of piezoelectric element 24, in which the original molecular imput to the piezoelectric element is augmented. Augmenting the vibrational force on the element 24 results in voltage of an increased magnitude flowing to the amplifier 66 to again be amplified. The voltage output from the amplifier 66, results by feed back in a repetition of the cycle above described in which increased vibrational energy is fed back to the piezoelectric element 24. The amplified voltage output from the piezoelectric element 24 results in voltage of sufficient magnitude being provided to actuate either the oscilloscope 68 to define a unique pattern inherant to the unknown substance B or to actuate the recording computer readout 70. The determination of the identity of the unknown substance B is achieved by comparing the pattern provided either on the oscilloscope or the recording computer readout 70 with the patterns of substances that have known identities.

The pivotal movement of the member 42 by use of the rod 52 is of the upmost importance, for as the rod 52 in conjunction with the spring 50 permits clockwise movement of the member 42, the grid C is forced into greater pressure contact with the forward membrane 140 The greater the pressure against the membrane the greater the rise in frequency thereof, and a lesser pressure of the grid C lowers the frequency ratio of the membrane vibration. By downward movement of the rod 58, the member 42 may be pivoted in a counter clockwise direction as viewed in FIG. 1 and the grid C separated from the forward disphram 140.

An alternate form A-1 of the invention is shown in FIGS. 5 to 9 inclusive that differs from the first form A only in that the grid C is eliminated as is the ring 136 and forward diaphram 140. The grid C is replaced by a paper thin brass reed 150 to which is soldered or otherwise secured a thin wire 152 that has a looped portion 154 that may be gripped between the clip assembly 28' and the piezoelectric element 24.

A cap 156 fits over the forward end of the tube 132, which cap has a centered, transverse tapped bore 158 therein. An externally threaded tubular nozzle 160 engages the tapped bore 158, which nozzle has an internal diameter substantially less than that of the tube 132.

The action of the nozzle 160 is similar to a Bernoulli tube action, where the reduction in the size of the tube increases the velocity of the vibrating air stream by resonance. The reed 150 is centered longitudinally with the interior of the nozzle 160. As the diaphram 142 vibrates pulses of air from the resonator cavity R are directed by the nozzle 160 onto the reed 150 to vibrate the latter and subject the piezoelectric element to vibrating mechanical forces.

The change from the grid C to the reed 150 restricts the harmonic nature of the output somewhat, but produces a better pattern on the recording computer readout 70. The pattern produced on the oscilloscope 68 is in many instances much too fast for the eye to follow visually, and leaves no comparative record for analysis.

The cross piece 30 is adjustably supported and permits the grid C or the reed 150 to be centered relative to the tube 132. Other than the differences above mentioned, the forms A and A-1 are identical. Elements in the form A-1 that are common to the form A of the invention are identified on the drawings by the same munerals but with primes added thereto.

It is well known that minute particles that have been electrostatically attracted to a body are dislodged therefrom when the body is subjected to a sharp impact. The spring loaded second rod 58 when lifted upwardly by handle 64 and then released impacts on arm 42b, with the shock of the impact being transferred through arms 42a to piezoelectric element 24, and molecules that have been attracted to the element being dislodged therefrom. Such dislodgement operation will be conducted by a user at the conclusion of a substance identifying operation.

The use and operation of the invention has been described previously in detail and need not be repeated.

What is claimed is:

1. An apparatus for detecting and identifying an unknown substance not common to the ambient atmosphere, said apparatus including:
   a. a housing that has a forward and rearward end;
   b. a piezoelectric element having an exterior surface;
   c. first means for supporting said piezoelectric element at a fixed position in said housing;
   d. force receiving means operatively associated with said piezoelectric element;
   e. second means for drawing a stream of air across said substance for surface active molecules of said substance to become entrained therewith, with said air stream containing said molecules being subsequently pressurized;
   f. third means for discharging said pressurized air stream across said exterior surface of said piezoelectric element until a substantial quantity of said molecules have accumulated on said exterior surface thereof by electrostatic attraction thereto to vibrate said piezoelectric element for the latter to generate a first voltage of the same frequency as that of said vibrations;
   g. electrically powered voltage amplifying means having a voltage imput and an amplified voltage output;
   h. a loud speaker that includes an armature and a cone;
   i. first electrical conducting means for delivering said first voltage to said imput;
   j. second electrical conducting means for delivering said amplified voltage from said amplifier to said armature to actuate said cone to emit pulsed sound waves;
   k. fourth means that vibrate in response to said pulsed sound waves;
   l. fifth means for transferring said vibrations of said fourth means to said force receiving means to augment the vibrating force to which said piezoelectric element is subjected by said molecules and increase the magnitude of said first voltage; and
   m. sixth means energized by the amplified voltage after said first voltage has been augmented, said sixth means indicating a frequency pattern that is related to the vibrations to which said piezoelectric element is subjected by said molecules, with said frequency pattern being destinctive for each of said substances being detected and identified.

2. An apparatus as defined in claim 1, in which said second means is a blower that has a suction and a discharge and an electric motor that drives said blower, said blower situated in said housing and said suction in communication with an opening in said forward end through which said air stream and molecules of said substance are drawn when said electric motor is energized, and said apparatus in addition including;
   n. an electric circuit that connects said electric motor to a source of electric power; and
   o. a normally open electric switch that forms a part of said electric circuit, said switch being placed in a closed position to energize said motor only for the time period required for said substantial quantity of said molecules to be electrostatically attracted to said piezoelectric element.

3. An apparatus as defined in claim 2, which in addition includes;
   p. seventh means for dislodging said molecules from said piezoelectric element after said substance has been detected and identified.

4. An apparatus as defined in claim 3, in which said seventh means is a spring loaded rod movably supported by said housing which rod may be manually manipulated to jar said piezoelectric element to displace said molecules therefrom.

5. An apparatus as defined in claim 1, in which said fourth and fifth means are longitudinally spaced rearward and forward resilient diaphrams, and said apparatus in addition including;
   n. a first tube having rearward and forward ends that are spanned by said rearward and forward diaphrams to define a resonator cavity with said rearward diaphram when vibrated by said pulsed sound waves causing said forward diaphram to vibrate, and vibrations of this forward diaphram being transferred as mechanical energy to said force receiving means.

6. An apparatus as defined in claim 5, in which said rearward and forward diaphrams are of different diameters and there is a non-linear relationship as to the rates that they vibrate relative to one another.

7. An apparatus as defined in claim 5, in which said force receiving means is a grid that extends rearwardly from said piezoelectric element and contacts said forward diaphram.

8. An apparatus as defined in claim 7, in which said piezoelectric element is movably supported in said housing, and said apparatus in addition including:
   o. manually adustable means for moving said piezoelectric element forwardly and rearwardly relative to said forward diaphram to permit the pressure said grid exerts thereon to be varied.

9. An apparatus as defined in claim 1, in which said force receiving element is a vibratable reed and said fourth means is a rearward diaphram, a first tube that has forward and rearward ends, with said rearward ends, with said rearward end spanned by said rearward diaphram, and said fifth means is a second tube of smaller diameter than said first tube and longitudinally disposed in said forward end of the latter, said second tube aligned with said reed, and said reed being subjected to pulses of air as said rearward diaphram vibrates by sound waves from said cone.

10. An apparatus as defined in claim 1, in which said sixth means is an oscilloscope.

11. An apparatus as defined in claim 1, in which said sixth means is a recording computer readout.

12. An apparatus as defined in claim 1, in which said piezoelectric element is a crystal phonograph pick-up cartridge.

* * * * *